United States Patent [19]

Black et al.

[11] Patent Number: 4,519,394
[45] Date of Patent: May 28, 1985

[54] METHOD AND APPARATUS FOR CATHODIC POTENTIAL CONTROL IN ELECTRICALLY INDUCED OSTEOGENESIS

[75] Inventors: Jonathan Black, King of Prussia; Thomas J. Baranowski, Jr., Philadelphia, both of Pa.

[73] Assignee: Trustees of the University of Pennsylvania, Philadelphia, Pa.

[21] Appl. No.: 472,567

[22] Filed: Mar. 7, 1983

[51] Int. Cl.$^3$ .............................................. A61N 1/20
[52] U.S. Cl. ................................................ 128/419 F
[58] Field of Search ............... 128/419 F, 419 R, 82.1

[56] References Cited

U.S. PATENT DOCUMENTS 3,842,841  10/1974  Brighton et al. ................. 128/419 F
3,848,608  11/1974  Leonard .......................... 128/419 R
4,026,304   5/1977  Levy .............................. 128/419 F

FOREIGN PATENT DOCUMENTS 643156  1/1979  U.S.S.R. .......................... 128/419 F

OTHER PUBLICATIONS

Zimmer USA "The Alternate Treatment of Fracture Nonunion-Electrical Stimulation to Induce Osteogenesis" Zimmer USA Sales brochure Lit No. B-2360-1, Sep. 1979.

Primary Examiner—William E. Kamm
Assistant Examiner—Mitchell J. Shein
Attorney, Agent, or Firm—Stevens, Davis, Miller & Mosher

[57] ABSTRACT

Disclosed is a method and apparatus for maintaining the potential between a cathode and a reference electrode substantially constant during electrically-induced osteogenesis. Two separate embodiments of electronic circuits are provided which will generate a D.C. current to flow between a cathode and anode while maintaining the potential between the cathode and the reference electrode substantially constant within the range of 0.1 to 1.26 Volts and preferably within the range of 1.0 to 1.26 Volts. Improvement in the amount of new bone grown over prior art bone growth stimulators is on the order of 200 to 300 percent. The electronic circuits provide the substantially constant cathodic potential over a wide range of load impedances between the anode and cathode. The disclosure is applicable not only to improving osteogenesis in bone fracture sites, but also to applications in which it is desirable to provide bone accretion for any reason.

10 Claims, 6 Drawing Figures

METHOD AND APPARATUS FOR CATHODIC POTENTIAL CONTROL IN ELECTRICALLY INDUCED OSTEOGENESIS

BACKGROUND OF THE INVENTION

The present invention relates generally to electrically-induced osteogenesis, and specifically to an improved method and apparatus for implementing the method of Direct Current stimulated osteogenesis.

The use of Direct Current of from between 5 and 20μ amperes applied to a cathode inserted into a fracture site and an anode taped to the skin location near the cathode implantation is well-known in the art and is discussed in detail in U.S. Pat. No. 3,842,841, issued to Brighton, et al., on Oct. 22, 1974. The insertion of a cathode into the fracture site and the providing of a small current flow from the cathode to an anode taped on the skin has been found quite effective in the stimulation of bone growth at the tissue site surrounding the cathode. As reported in the *Journal of Bone and Joint Surgery.* Volume 62-A, No 1, pages 2–13, in January of 1981: "A Multi-Center Study of the Treatment of Non-Union With Constant Direct Current", a success rate of around 80 per cent was obtained in stimulating bone growth among patients having broken bones which had not mended over a substantial period of time.

In an abstract entitled "Electrically-Induced Osteogenesis: Relationship of Current Density to Quantity of Bone Formed", by Brighton, et al. published with the 24th Annual ORS (Orthopaedic Research Society), page 30, Feb. 21–23, 1978, it was found that the size of the "port" (the exposed cathode/tissue interface) should be at least 0.11 mm$^2$ in area. However, the study also indicated that a cathode with multiple ports can distribute a much higher amount of Direct Current into a tissue site and stimulate a larger amount of bone growth therein. The above references are herein incorporated by reference.

Currently, systems are marketed by ZIMMER·USA, of Warsaw, Ind., 46580, which provide a constant current (±5%) power which is supplied to either separate cathodes or a single cathode with multiple ports. FIG. 1 illustrates such prior art systems. Bone 10 has been fractured in the vicinity of tissue site 12, which is surrounded by living tissue 14 covered by skin 16. A cathode 18 having a single port 20 is inserted such that the port is in the vicinity where osteogenesis is to be stimulated. A surface anode 22 is placed in contact with the skin 16 and anode lead 24 and the cathode 18 are electrically connected to a constant current power supply 26. In the preferred embodiment, since there is only a single port at the tissue site 12, the power supply would produce 20 μ amps to produce the maximum amount of bone growth at the tissue site without incurring necrosis at either the tissue site or the anode/skin interface.

Even though such prior art Direct Current systems have a demonstrated capability to induce bone growth in living tissue, the amount of bone growth appears to vary from animal to animal or case to case, even though the current level between the cathode and the anode has been maintained at the believed optimum level of 20μ amps.

SUMMARY OF THE INVENTION

It is therefore an object of the present invention to provide a method and an apparatus for maintaining osteogenic stimulation at an optimum or near-optimum level over an extended period of time.

It is a further object of the present invention to provide a method and apparatus for improving bone growth stimulation over that achievable in prior art bone growth stimulators.

It is a further object of the present invention to provide a method and apparatus for maintaining a current in the range of from 0.1 to 100μ amps per cathode port and for maintaining the cathode port-to-body reference voltage substantially constant in the range of from 0.1 to 1.26 Volts.

The above and other objects are achieved in accordance with the present invention by providing a reference electrode located in the living tissue remote from the cathode and anode location. The cathode-to-reference electrode voltage is monitored and maintained within the range of from 0.1 to 1.26 Volts, while the power pack connected to the cathode, anode, and reference electrode maintains the cathode-to-anode current substantially constant in the range of from 5 to 20μ amps. In one embodiment, two batteries are connected in series with a four-resistor voltage divider with the direct connection between the two batteries also connected to between the two pairs of resistors. The direct connection between the junction of the two batteries and the junction of the two pairs of resistors is connected to a reference electrode located in the living tissue remote from the cathode location. One of the pairs of resistors has the series junction between the resistors connected to the base of an NPN transistor, whose emitter is coupled to the anode and whose collector is coupled through a limiting resistor to the respective battery. The other pair of resistors has its series junction connected to the base of a PNP transistor, whose emitter is coupled to the cathode and whose collector is coupled through a current limiting resistor to the other battery.

In a further preferred embodiment, operational amplifiers may be substituted for the transistors and an adjustable potentiometer substituted for each of the resistor pairs. This embodiment produces better voltage control at lower voltages, but requires a higher amp/hour battery rating than does the transistor embodiment.

BRIEF DESCRIPTION OF THE DRAWINGS

A more complete appreciation of the invention, and many of the attendant advantages thereof, will be readily apparent by reference to the accompanying Drawings, wherein.

DETAILED DESCRIPTION OF PREFERRED EMBODIMENTS

Figure 3:
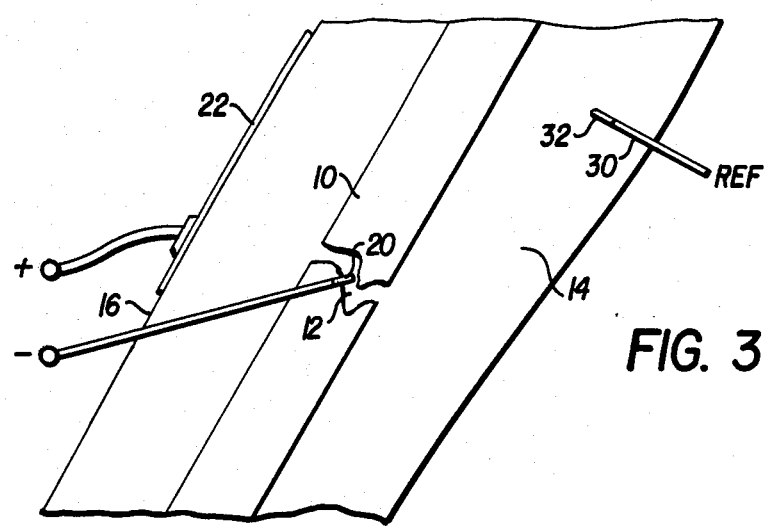
FIG. 3 is a side representational view showing the insertion of cathode and reference electrodes and the placement of an anode in accordance with the present invention.

Referring now more particularly to the Drawings, wherein like numerals represent like elements throughout the several views, FIG. 3 illustrates a single port cathode 18 and a mesh anode 22. Although platinum and silver have been used along with other materials as cathodes, a preferred embodiment of the present invention utilizes a stainless steel cathode having a single port. The stainless steel cathode is coated with an insulator, in a preferred embodiment, PTFE, so as to provide a cathode/tissue interface only at the port 20.

The anode may be constructed of platinum, silver, or titanium, among other materials, and could be surgically implanted if desired. However, in a preferred embodiment, the anode is an electrode fabricated with a chloride of silver conductor and an unfilled, high conductivity electrolyte gel maintained in contact with the skin 16 of the patient.

An additional reference electrode 30 has a reference electrode port 32 inserted into the living tissue 14 at a point remote from the cathode and anode locations.

For the purpose of this specification and claims, the term "biocompatible material" means a material which shows an acceptable, acute and chronic local tissue response. Additionally, "substantially constant" refers to voltage variations of less than ±5%.

Figure 1:
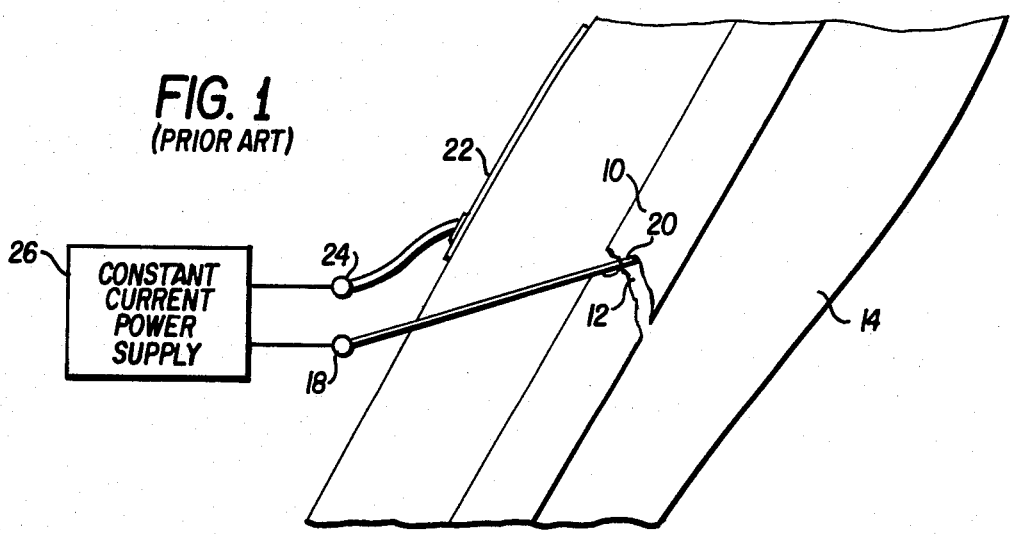
FIG. 1 is a side representational view of a prior art osteogenesis inducing power supply and electrodes.
Figure 2:
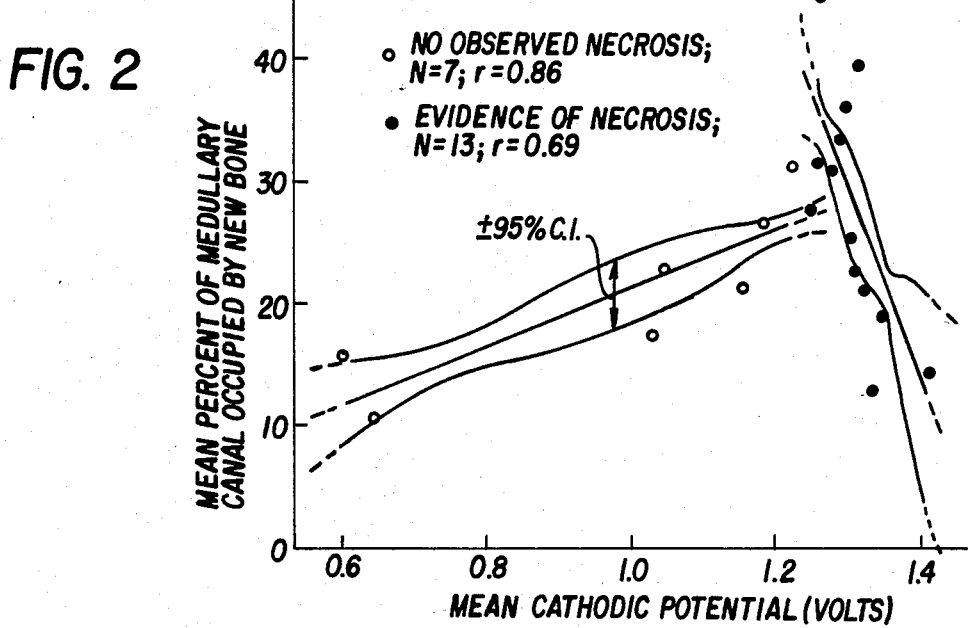
FIG. 2 is a graph of new bone versus cathodic potential.

FIG. 2 illustrates the results of experiments conducted by the inventors in which the cathodic potential varies (the potential between the cathode and a reference electrode comprised of Ag/AgCl). The tests were conducted in order to stimulate new bone growth in the medullary canal of test rabbits. A Direct Current of 20μ Amps was utilized with a variety of cathodes and the cathodic potential was monitored three times a week. After three weeks of Direct Current stimulation, the rabbit tibias were excised and the percentage of the medullary canal cross-section containing new bone growth analyzed by pairwise linear regression among parameters including mean cathodic potential, cathode diameter, mean percentage new bone, and other factors. The graph in FIG. 2 illustrates that there is no correlation between mean cathodic potential and electrically-stimulated osteogenesis if only new bone is considered, since relatively low and relatively high cathodic potentials produced on the order of 10 percent new bone growth. However, if bone growth data for animals in which no necrosis was observed is separately considered, then a significant positive correlation is observed between mean cathodic potential and osteogenesis. Further, if bone growth data for animals in which some necrosis was observed is separately considered, then a significant negative correlation is observed between mean cathodic potential and osteogenesis (the first correlation—the non-necrosis region—is the region of clinical interest). As can be seen, the amount of bone growth increases with no observed necrosis until the potential reaches 1.26 Volts, where osteogenesis decreases and is replaced by various degrees of necrosis. The statistical confidence interval of ±95 percent indicates that there is a legitimate trend towards higher bone growth at the higher potentials (up to 1.26 Volts). This view is substantiated by the fact that both regression coefficients are highly significant.

It has been determined that the bone growth stimulation can be increased by up to 300 percent by the appropriate cathodic potential and up to at least 200 per cent over the prior art optimum of 20μ Amps per port without cathodic potential control. There has been devised an electronic circuit shown in FIG. 4 which is capable of providing a desirable substantially constant cathodic potential while delivering a desired level of current (in a preferred embodiment 20μ Amps per port). The outputs with the plus connected to the anode, the minus connected to the cathode, and the REF connected to the reference electrode, can be characterized by anode current $I_A$, reference current $I_R$, and cathode current $I_C$. The interelectrode voltages are identified as $V_{RA}$ (reference-to-anode), $V_{AC}$ (anode-to-cathode), and $V_{RC}$ (reference-to-cathode, the cathodic potential of interest).

Figure 4:
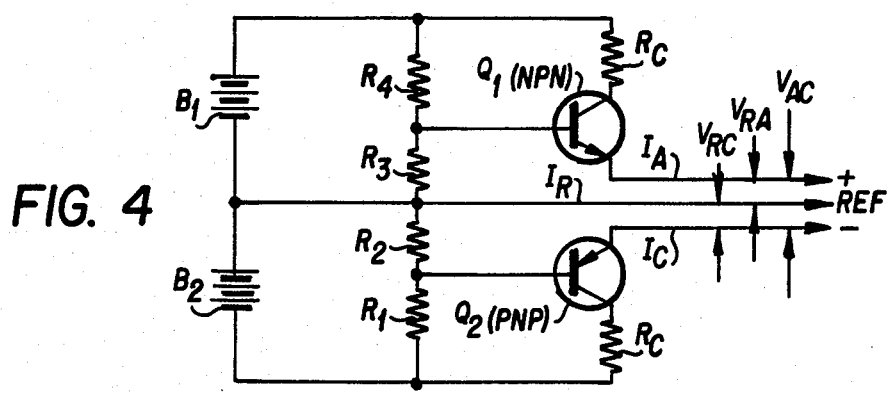
FIG. 4 is an electrical schematic of one embodiment of the Direct Current power supply in accordance with the present invention.

Batteries B1 and B2 in the FIG. 4 embodiment are 7-Volt mercury cells connected in series. Each battery is connected to a voltage divider comprised of a pair of resistors R3 and R4 with battery B1 and R1 and R2 with battery B2. The voltage divider formed by resistors R4 and R3 has the lower end connected directly to the reference electrode and the upper end connected through a current limiting resistor $R_C$ to the collector of transistor Q1. In the illustrated embodiment, Q1 is an NPN-type transistor No. 2N3904 and the base of the transistor is connected to the terminal joining resistors R3 and R4. Similarly, the voltage divider formed in the resistors R1 and R2 are connected between the reference electrode and a second load resistor $R_C$ also having a resistance of 6.8 KOhms. The second load resistor is connected to the collector of a PNP-type transistor Q2 with a number 2N3906, whose emitter is coupled to the cathode. The base of transistor Q2 is connected to the junction between resistors R1 and R2. By changing the ratio of R3 to R4 and R1 to R2, the base bias of transistors Q1 and Q2 can be varied, thus adjusting the current flow and cathodic potential of the circuit. Table 1 illustrates typical current and $V_{RC}$ values obtained with the circuit connected to a "glass rabbit" when R1 and R2 are changed with R3=56 KOhms and R4=420 KOhms. As can be seen, the reference current $I_R$ is maintained at a minimum, even though the anode and cathode currents can be varied quite substantially. Obviously, the cathodic potential can be adjusted over a considerable range, which more than exceeds the maximum desired cathodic potential of 1.26 Volts.

| $V_{RC}$ | $I_R$ | $I_C$ | $I_A$ | R$_1$ | R$_2$ |
| --- | --- | --- | --- | --- | --- |
| .793 V | −0.4 μA | 31 μA | −32 μA | 400 KΩ | 100 KΩ |
| .919 V | 0.2 μA | 64 μA | −63 μA | 420 KΩ | 114.9 KΩ |
| 1.084 V | 0.6 μA | 72 μA | −70 μA | 129 KΩ | 42 KΩ |
| 1.375 V | 3.4 μA | 120⇌128 μA | −120⇌−125 μA | 900 KΩ | 400 KΩ |

Therefore, in order to obtain maximum bone growth stimulation, one might utilize the FIG. 4 circuit with the ratio of $R_1$ to $R_2$ of approximately 2.75 and substitute resistances of $R_1$=100 KΩ and $R_2$ of 36 KΩ. This would also produce a cathode current on the order of 80μ Amps which could be distributed to the living tissue by means of 4 cathode ports, either all in one cathode electrode or in four separate single port cathode electrodes. Studies have not been completed to determine if Direct Current levels should be maintained within certain ranges in order to achieve the full benefits of a constant potential. Therefore, as long as $V_{RC}$ was in the desired range (from 0.1 to 1.26 Volts), bone growth would be stimulated accordingly.

Figure 5:
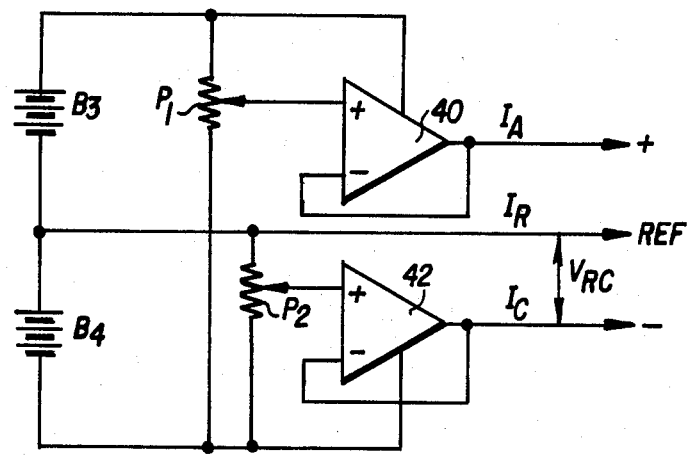
FIG. 5 is a further embodiment of the Direct Current power supply.

The FIG. 4 circuit provides a satisfactory level of current drain at $V_{RC}$ of 0.8 Volts and higher. A relatively low current drain indicates that there is no difficulty with regard to power supply durability during a 21-day operation in the event it is desirable to implant the Direct Current power source under the skin. Where a lower cathodic potential is required and current drain is not critical (in the instance of an externally mounted power supply), a circuit, as shown in FIG. 5, has been found very effective.

Operational amplifiers 40 and 42 are of the LM741 type and they are connected as a follower amplifier having a gain of unity. Batteries B3 and B4 are 9-Volt alkaline batteries with potentiometer P1 having a total resistance of 50 KΩ being connected across both batteries while potentiometer P2 having a total resistance of 10 KΩ is connected only across battery B4. By adjusting the potentiometers P1 and P2, the voltages and currents shown in Table 2 were obtained.

TABLE 2

| $V_{RC}$ | $I_R$ | $I_C$ | $I_A$ |
| --- | --- | --- | --- |
| .100 V | 0.3 μA | −4.1⇌−4.6 μA | 3.8⇌4.2 μA |
| .300 V | 0.13 μA | 10⇌10.8 μA | −10.4⇌−11 μA |
| .500 V | 0.5 μA | 24⇌26 μA | −23⇌−25 μA |
| .850 V | 0.4⇌0.9 μA | 40⇌50 μA | −40⇌−50 μA |
| 1.000 V | 0.2⇌0.9 μA | 47⇌60 μA | −48⇌−61 μA |

Note that with the FIG. 5 circuitry, when $V_{RC}$ is equal to 0.100 Volts, the cathode current and the anode current are actually reversed and current flows from the anode towards the cathode. By slightly adjusting potentiometers P1 and P2 to increase the reference electrode current, this tendency can be eliminated. Testing of the FIG. 5 circuitry indicated that while it had exceptional $V_{RC}$ control independent of the load between the anode and cathode, it had a relatively high drain of 2.2 mA, thus requiring a fairly substantial battery pack in order to last twenty-one days, a typical period for an implanted bone growth stimulator. However, such a device could be powered externally with percutaneous skin connectors or with a radio frequency transmitter and receiver power supply system.

Figure 6:
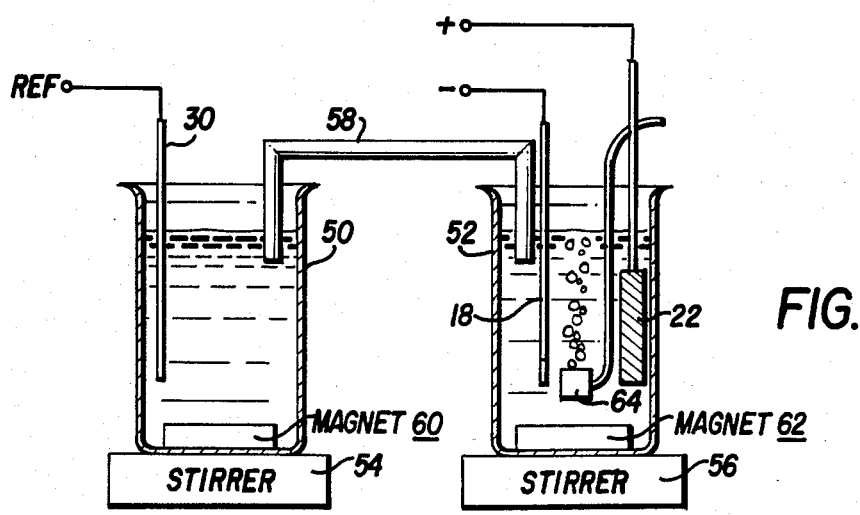
FIG. 6 is a side cross-sectional view of a test apparatus for determining the operational characteristics of constant current power supplies in accordance with the present invention.

The circuits of FIGS. 4 and 5 were tested on a "glass-rabbit", which approximated the electrical characteristics of a test animal. Such a "glass-rabbit" is shown in FIG. 6. Two beakers 50 and 52 were set on hotplate stirrers 54 and 56 (Corning PC-351), respectively, one containing a reference electrode 30 and the other containing the anode 22 and the cathode 18. Here, the reference electrode used was an implantable Ag/AgCl electrode. The anode was a grid-like stainless steel mesh and the cathode was a 26-gauge stainless steel electrode covered with PTFE, with the exception of a 1-centimeter bare tip. The beakers were connected by a salt bridge 58. Magnets 60 and 62 rotated under the influence of stirrers 54 and 56, respectively, to circulate a 0.9% Normal saline solution in the beakers. An air stone 64 (otherwise known as a bubbler) is supplied with air under pressure from an external source (not shown) and serves to oxygenate the saline solution. The tests were all run at room temperature, since temperature was not believed to be a critical factor in the electronic operation. The results discussed in Tables 1 and 2 were obtained by connecting the circuits of FIGS. 4 and 5, respectively, to the FIG. 6 circuitry.

The Applicants have clearly determined that there is a definite relationship between bone growth and the cathodic potential used in stimulation of bone growth. The anode/cathode current may be an additional factor in optimization, but it has clearly been shown that substantial increases in bone growth can be achieved by utilizing substantially constant cathodic potentials on the order of 0.1 to 1.26 Volts and particularly in the range of from 1.0 to 1.26 Volts. Two circuits have been discussed which will meet the minimum requirements of providing a substantially constant cathodic potential over widely varying load ranges (the impedance between the anode and the cathode). Testing of these circuits in live animals may demonstrate to those of ordinary skill in the art that variations and modifications of the circuitry will be necessary in order to maintain the desired cathodic potential in vivo. Therefore, many circuits providing a substantially constant cathodic potential will be obvious to those of ordinary skill in the art, in view of the above disclosures, and can be utilized to provide the beneficial osteogenesis stimulation as discussed above. Many factors, such as cost, manufacturing complexity, use of implanted batteries as opposed to an external power source, the number of cathode ports, size, weight, etc., will govern the particular substantially constant cathodic potential circuit to be chosen for a particular application. However, these circuits obvious to those of ordinary skill in the art, in view of the above disclosure, are contended to be within the scope of the present invention. Similarly, the choice of a specific cathode, anode, or reference electrode may be governed by the patient, the skin condition, cost, manufacturing complexity, and other factors, and as such all of the various combinations are believed included within the scope of the present invention.

Thus, in view of the above teachings, modifications of the circuits in FIGS. 4 and 5 will become obvious to those of ordinary skill in the art. Therefore, the present invention is not limited to those embodiments and/or the applications expressed herein. Because it is desirable to stimulate bone growth in certain situations other than the case of fractures (the promotion of tooth movement, the closure of a cleft palate or building up the alveolar bone ridge as disclosed in Korostoff, et al., U.S. Pat. No. 4,153,060, issued May 8, 1979), it is believed that the invention can be utilized to stimulate osteogenesis at any suitable tissue site in living tissue with a variety of cathode/anode/reference electrode combinations (including surface electrodes) as long as the cathodic potential is maintained in the desirable range. Therefore, the present invention is limited only in accordance with the appended claims.

What is claimed is:

1. A method of stimulating osteogenesis at a tissue site in living tissue internal to a skin surface, said method comprising the steps of:

providing an anode, a cathode, and a reference electrode;

locating said cathode at said tissue site, said anode in contact with said living tissue and said reference electrode in contact with said living tissue remote from said tissue site; and applying a direct current from said cathode to said anode and maintaining a potential between said cathode and said reference electrode substantially constant.

2. The method according to claim 1, wherein said applying and maintaining step comprises maintaining the potential between said cathode and said reference electrode substantially constant in the range of from 0.1 to 1.26 Volts.

3. The method according to claim 2, wherein said locating step includes locating said anode on said skin surface.

4. The method according to claim 3, wherein said cathode has at least one port and said applying step comprises applying a direct current in the range of from 0.1 to 100 µA per port between said cathode and said anode.

5. The method according to claim 3, wherein said applying step comprises maintaining the potential between said cathode and said reference electrode substantially constant in the range of from 1.0 to 1.26 Volts.

6. An apparatus for providing direct current for stimulating osteogenesis at a tissue site associated with living tissue, said apparatus comprising:
a cathode means for electrically contacting said living tissue;
an anode means in contact with said living tissue;
reference electrode means in contact with said living tissue remote from said cathode means and said anode means;
means, connected to said cathode means, anode means, and reference electrode means, for generating a direct current at least between said cathode means and anode means and for maintaining a substantially constant potential between said cathode means and said reference electrode means.

7. The apparatus according to claim 6, wherein said generating and maintaining means comprises means for maintaining a substantially constant potential between said cathode means and said reference electrode means in the range of from 0.1 to 1.26 Volts.

8. The apparatus according to claim 7, wherein said living tissue includes a skin surface and said tissue site is internal to said skin surface, said cathode means including means insertable into said living tissue, said anode means comprising electrically conductive anode means located on said skin surface, and said reference electrode means comprises means insertable into said living tissue.

9. An apparatus according to claim 8, wherein said cathode means includes at least one port located in the vicinity of said tissue site and said generating means generates a direct current in the range of from 0.1 to 100 µA per cathode port.

10. An apparatus according to claim 8, wherein said generating and maintaining means includes means for maintaining substantially constant a potential between said cathode and said reference in the range of from 1.0 to 1.26 Volts.

* * * * *